(12) United States Patent
Kawde et al.

(10) Patent No.: US 9,851,325 B2
(45) Date of Patent: Dec. 26, 2017

(54) CATHODIZED GOLD NANOPARTICLE GRAPHITE PENCIL ELECTRODE AND METHOD FOR GLUCOSE DETECTION

(71) Applicants: KING FAHD UNIVERSITY OF PETROLEUM AND MINERALS, Dhahran (SA); KING ABDULAZIZ CITY FOR SCIENCE AND TECHNOLOGY, Riyadh (SA)

(72) Inventors: Abdel-Nasser Metwally Aly Kawde, Dhahran (SA); Md. Abdul Aziz, Dhahran (SA)

(73) Assignees: KING FAHD UNIVERSITY OF PETROLEUM AND MINERALS, Dhahran (SA); KING ABDULAZIZ CITY FOR SCIENCE AND TECHNOLOGY, Riyadh (SA)

( * ) Notice: Subject to any disclaimer, the term of this patent is extended or adjusted under 35 U.S.C. 154(b) by 308 days.

(21) Appl. No.: 14/719,940

(22) Filed: May 22, 2015

(65) Prior Publication Data
US 2015/0253278 A1     Sep. 10, 2015

Related U.S. Application Data

(62) Division of application No. 14/042,419, filed on Sep. 30, 2013, now abandoned.

(51) Int. Cl.
*C25D 5/48*      (2006.01)
*G01N 27/327*    (2006.01)
(Continued)

(52) U.S. Cl.
CPC .......... *G01N 27/327* (2013.01); *G01N 27/30* (2013.01); *G01N 27/308* (2013.01);
(Continued)

(58) Field of Classification Search
CPC .... G01N 27/327; G01N 27/30; G01N 27/308; G01N 27/3278; G01N 27/48; G01N 27/3277; C25D 5/48
See application file for complete search history.

(56) References Cited

U.S. PATENT DOCUMENTS 8,083,926 B2    12/2011 Chen
2009/0090623 A1    4/2009 Chuang et al.

OTHER PUBLICATIONS

Burke et al., Generation of active surface states of gold and the role of such states in electrocatalysis, (2000), J. Solid State Electrochem 4: pp. 285-297.*

(Continued)

*Primary Examiner* — Arun S Phasge
(74) *Attorney, Agent, or Firm* — Oblon, McClelland, Maier & Neustadt, L.L.P.

(57) ABSTRACT

The cathodized gold nanoparticle graphite pencil electrode is a sensitive enzymeless electrochemical glucose sensor based on the cathodization of AuNP-GPE. Cyclic voltammetry shows that advantageously, the cathodized AuNP-GPE is able to oxidize glucose partially at low potential (around −0.27 V). Fructose and sucrose cannot be oxidized at <0.1 V, thus the glucose oxidation peak at around −0.27 V is suitable enough for selective detection of glucose in the presence of fructose and sucrose. However, the glucose oxidation peak current at around −0.27 V is much lower which should be enhanced to obtain low detection limit. The AuNP-GPE cathodization increases the oxidation peak current of glucose at around −0.27 V. The dynamic range of the sensor is in the range between 0.05 to 5.0 mM of glucose with good linearity ($R^2$=0.999). Almost no interference effect was observed for sensing of glucose in the presence of fructose, sucrose and NaCl.

10 Claims, 11 Drawing Sheets

(51) Int. Cl.
*G01N 27/30* (2006.01)
*G01N 27/48* (2006.01)

(52) U.S. Cl.
CPC ..... *G01N 27/3278* (2013.01); *G01N 27/3277* (2013.01); *G01N 27/48* (2013.01)

(56) References Cited

OTHER PUBLICATIONS

J. Das, S. Patra, H. Yang "Enhancement of the electrocatalytic activity of gold nanoparticles via NaBH4 treatment" Chem. Commun. 2008, pp. 4451-4453.

Kyungmin Jo, Hyun Ju Kang, and Haesik Yang "Enhancement of the Electrocatalytic Activity of Gold Nanoparticles via Anodic Treatment and the Decrease of the Enhanced Activity with Aging" Bull. Korean Chem. Soc. 2011, vol. 32, No. 2, pp. 728-730.

Bai, Yu et al., "Enzyme-Free Glucose Sensor Based on a Three-Dimensional Gold Film Electrode," *Sensors and Actuators B: Chemical*, 134(2), pp. 471-476, 2008 (Abstract only).

Lu, Jue et al., "Nanometal-Decorated Exfoliated Graphite Nanoplatelet Based Glucose Biosensors with High Sensitivity and Fast Response," *ACS Nano*, 2(9), pp. 1825-1832, 2008.

Myung, Yoon et al., "Nonenzymatic Amperometric Glucose Sensing of Platinum, Copper Sulfide, and Tin Oxide Nanoparticle-Carbon Nanotube Hybrid Nanostructures," *Journal of Physical Chemistry C*, 113(4), pp. 1251-1259, 2009 (Abstract only).

Pasta, M. et al., "Alkaline Glucose Oxidation on Nanostructured Gold Electrodes" *Gold Bulletin*, 43(1), pp. 57-64, 2010.

Wojnicki, Marek et al., "Electro-Oxidation of Glucose in Alkaline Media on Graphene Sheets Decorated with Gold Nanoparticles," *Materials Sciences and Applications*, 4, pp. 162-169, 2013.

Zhu, Hong et al., "Nortenzymatic Glucose Voltammetric Sensor Based on Gold Nanoparticles/Carbon Nanotubes/Ionic Liquid Nanocomposite," *Talanta*, 79(5), pp. 1446-1453, 2009.

\* cited by examiner

CATHODIZED GOLD NANOPARTICLE GRAPHITE PENCIL ELECTRODE AND METHOD FOR GLUCOSE DETECTION

CROSS REFERENCE TO RELATED APPLICATION

This application is a division of application Ser. No. 14/042,419, filed Sep. 30, 2013, now pending.

BACKGROUND OF THE INVENTION

1. Field of the Invention

The present invention relates to glucose sensors, and particularly to an enzyme-free cathodized gold nanoparticle graphite pencil electrode (GPE) based glucose sensor and methods for glucose detection.

2. Description of the Related Art

Glucose is an important molecule for human, plant and other living organisms. However, the presence of lower or higher concentration of dissolved glucose in blood outside of the normal range (4.4-6.6 mM) is the symptom of diseases "Diabetes mellitus". As a result, knowing the exact glucose level in blood is crucial for diagnosis and management of Diabetes mellitus. Moreover, glucose is used in several industries such as textile, pharmaceuticals, food industries including beverages, renewable and sustainable fuel cells, and the like. Therefore, a simple, disposable, cheap, selective and sensitive glucose sensor is required for continuous glucose monitoring.

Among the common analytical methods, the electrochemical method has been widely appreciated due to its simplicity, portability, selectivity and sensitivity. Generally, electrochemical glucose sensors are classified as either (i) enzyme base glucose sensor or (ii) nonenzymatic glucose sensor. Expensive enzyme and complicated enzyme immobilization methods are required for fabrication of enzyme based electrochemical glucose sensors. Moreover, $H_2O_2$ is produced in the enzyme base glucose sensor from glucose and the produced $H_2O_2$ is oxidized on the electrode surface to generate a signal for the glucose. Practically, for oxidation of $H_2O_2$ there is typically required a potential which is high enough to oxidize interference (e.g. fructose, sucrose, ascorbic acid, dopamine uric acid etc.) in the real sample.

To overcome those problems, a plethora of nonenzymatic glucose sensors have been developed. A nonenzymatic glucose sensor depends on a direct glucose oxidation signal on the electrode surface and their selectivity depends on the oxidation potential of glucose. Nanoparticles of both transition and noble metals have been used to enhance the electrocatalytic properties of a substrate electrode toward glucose oxidation. For example, gold nanowire array electrode, gold nanoparticles (Au NPs)-modified amine-functioned mesoporous silica films on glassy carbon electrode (GCE), CoOOH nanosheet-modified cobalt electrode, bimetallic Pt-M (M=Ru and Sn) NPs on carbon nanotube (CNT)-modified GCE, Pt/Ni—Co nanowires, Pd NPs on graphene oxide, Au NPs on polypyrrole nanofibers-modified GCE, copper NPs on CNT-modified GCE, Au NP-modified nitrogen-doped diamond-like carbon electrodes, AuNP/carbon nanotubes/ionic liquid nanocomposite, and Au NP-modified indium tin oxide were used to direct oxidation of glucose.

Glucose can be partially oxidized at a bulk Au electrode or a nano gold electrode at lower potential which is required to eliminate the interferences effect for detecting glucose in a real sample. However, the signal of partial oxidation of glucose in alkaline medium at Au electrode is lower than that of full oxidation at high potential. It is known that the high signal is required to obtain low detection limit in an electrochemical sensor, and that the cathodization of an Au immaterial based electrode before recording an electrochemical signal can enhance the electrochemical signal of the analyte. The reasons of limited use of Au electrode for routine analysis of glucose are high price of gold, complex preparation method of nano gold or nano gold-modified electrode and low signal at low potential.

Moreover, the graphite pencil electrode (GPE) is an attractive electrode material because it is cheap, available, possesses an easy to make renewable surface, and is relatively stable. However, graphite typically shows poor electrocatalytic properties toward many electroactive molecules. The poor electrocatalytic properties of GPE should be improved to obtain a lower detection limit in electrochemical sensors.

Thus, a cathodized gold nanoparticle graphite pencil electrode addressing the aforementioned problems is desired.

SUMMARY OF THE INVENTION

Embodiments of a cathodized gold nanoparticle graphite pencil electrode (AuNP-GPE) provide a highly sensitive enzymeless electrochemical glucose sensor that is based on the cathodized gold nanoparticle-modified graphite pencil electrode (AuNP-GPE). By combining the advantages of AuNP, GPE and cathodization, embodiments of an AuNP-GPE provide for the fabrication of a nonenzymatic highly selective and relatively sensitive, cheap and disposable glucose sensor. The AuNP-GPE after cathodization at an optimum condition shows relatively a high selectivity, a low detection limit (12 micromolar (μM)) and a wide dynamic range (0.05-5 millimolar (mM)) toward glucose sensing. The cyclic voltammetry (CV) experiments show that embodiments of an AuNP-GPE can oxidize glucose partially at low potential (around −0.27 volts (V)), whereas the bare GPE generally cannot oxidize glucose in the entire tested potential windows, and that fructose and sucrose generally cannot be oxidized at <0.1 V at an AuNP-GPE. As a result, the glucose oxidation peak at around −0.27 V is relatively suitable enough for selective detection of glucose in the presence of fructose and sucrose.

However, the glucose oxidation peak current at around −0.27 V is typically much lower which should be enhanced to obtain a low detection limit. To increase the oxidation peak current of glucose at around −0.27 V, embodiments of an AuNP-GPE have been cathodized under relatively optimum condition (−1.0 V for 30 seconds (s)) in the same glucose solution before recording cyclic voltammetry (CV). This cathodization of an AuNP-GPE enhances the glucose signal and can allow a detection limit of 12 μM of glucose, for example. The dynamic range of embodiments of a glucose sensor using embodiments of a cathodized AuNP-GPE are typically in the range between 0.05 to 5.0 mM of glucose with relatively good linearity ($R^2=0.999$). Also, no significant interference effect was observed for the sensing of glucose in the presence of fructose, sucrose and NaCl.

These and other features of the present invention will become readily apparent upon further review of the following specification and drawings.

BRIEF DESCRIPTION OF THE DRAWINGS

Unless otherwise indicated, similar reference characters denote corresponding features consistently throughout the attached drawings.

DETAILED DESCRIPTION OF THE PREFERRED EMBODIMENTS

Figure 1A:
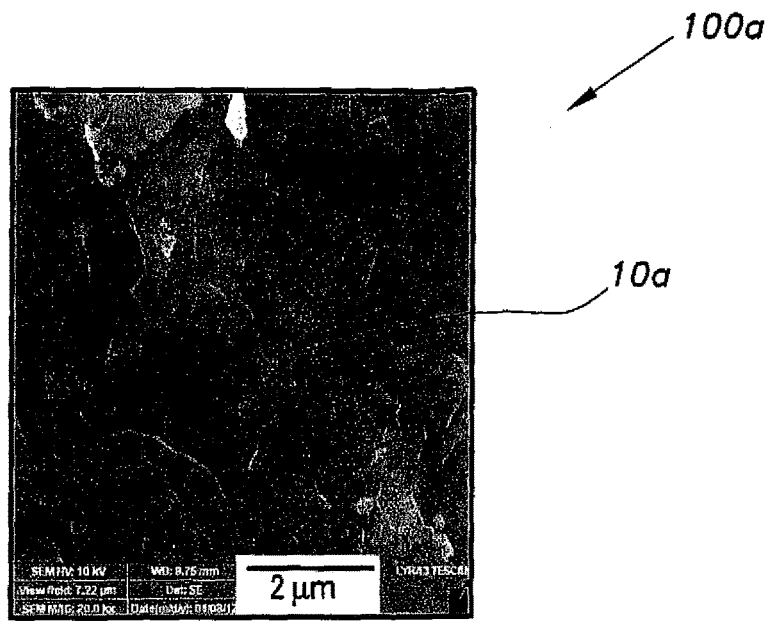
FIG. 1A is a Field Emission Scanning Electron Microscope (FE-SEM) image at 2 μm for a known bare graphite pencil electrode (GPE).

Embodiments of a cathodized gold nanoparticle graphite pencil electrode (AuNP-GPE) 10b (shown in FIGS. 1B and 1D in the micrographs 100b and 100d, respectively) provides a relatively highly sensitive enzymeless electrochemical glucose sensor based on a cathodized gold nanoparticle-modified graphite pencil electrode (AuNP-GPE). Performing the cyclic voltammetry (CV) experiments show that embodiments of an AuNP-GPE can oxidize glucose partially at a relatively low potential (around −0.27 V), whereas the bare GPE 10a (shown in FIGS. 1A and 1C in the micrographs 100a and 100c, respectively) typically cannot oxidize glucose in the entire tested potential windows. Besides, fructose and sucrose generally cannot be oxidized at <0.1 V at an AuNP-GPE. As a result, the glucose oxidation peak at around −0.27 V is generally suitable enough for selective detection of glucose in the presence of fructose and sucrose, for example.

However, the glucose oxidation peak current at around −0.27 V is much lower which should be enhanced to obtain a low detection limit. To increase the oxidation peak current of glucose at around −0.27 V, the embodiments of an AuNP-GPE have been cathodized under a relatively optimum condition (−1.0 V for 30 s) in the same glucose solution before performing and recording cyclic voltammetry (CV). This cathodization enhances the glucose signal and allows for a glucose detection limit of 12 μM, for example. The dynamic range of the sensor is in the range between 0.05 to 5.0 mM of glucose with a relatively good linearity ($R^2$=0.999). Also, no significant interference effect was observed for sensing of glucose in the presence of fructose, sucrose and NaCl, for example.

With respect to reagents used in relation to preparation of embodiments of an AuNP-GPE, Gold(III) chloride hydrate, D-(+) Glucose, D-(−) Fructose, Sucrose, L-ascorbic acid (AA), Sodium chloride and Sodium hydroxide were received from Sigma Aldrich. As to an example of graphite used in relation to preparation of embodiments of an AuNP-GPE, hi-polymer graphite pencil HB (grade) black leads were obtained from Pentel Co. LTD. (Japan). All leads had a total length of 60 millimeters (mm) and a diameter of 0.5 mm, and were used as received. All solutions were prepared with deionized water of a resistivity of 18.6 megaohms/centimeter (MΩ/cm), which was obtained directly from PURELAB® Ultra Laboratory Water Purification System.

A Jedo mechanical pencil (Korea) was used as a holder for both bare and AuNP-modified graphite pencil leads. Electrical contact with the lead was achieved by soldering a copper wire to the metallic part that holds the lead in place inside the pencil to provide an electrically conductive holder. The pencil lead was fixed vertically with 15 mm of the pencil lead extruded outside, and 10 mm of the lead immersed in the solution. Such length corresponds to a geometric electrode area of 15.90 mm². CH Instruments Inc. instrumentation was used for the electrochemical work in relation to embodiments of an AuNP-GPE. The electrochemical cell contained a bare GPE or an AuNP-GPE as a working electrode, a Pt wire counter electrode and Ag/AgCl (Sat. KCl) reference electrode. Before recording each voltammogram, argon gas was bubbled for 30 minutes (min) to remove oxygen from the solution. The FE-SEM images were recorded using TESCAN LYRA 3 at Center of Research Excellence in Nanotechnology (CENT), King Fand University of Petroleum and Minerals (KFUPM), Kingdom of Saudi Arabia.

With respect to embodiments of preparation methods of an AuNP-GPE, briefly, initially equal volumes (1.5 milliliters (ml) of each aqueous solutions) of 1.65 mM AA and 1.0 mM Gold(III) chloride were mixed using a pipette at room temperature (RT) in a 3.0 ml test tube to form gold nanoparticles (AuNPs). A bare GPE was immersed into that test tube, which was placed into a water bath preheated to 75° centigrade (C) and kept for 15 min to obtain the AuNP-GPE. Afterward, the AuNP-GPE was removed and washed by gentle dipping two times in deionized water, then dried at 60° C. for 5 min prior to use. The prepared AuNP-GPE was then cathodized by placing the AuNP-GPE in a glucose analyte solution and applying −1.0 volt to the AuNP-GPE for approximately 30 seconds to provide a cathodized AuNP-GPE. Also, the prepared AuNP-GPE can also be cathodized by placing the AuNP-GPE in a basic solution, such as in a 0.1 molar (M) NaOH, at −1.0 V for 30 seconds.

Figure 1B:
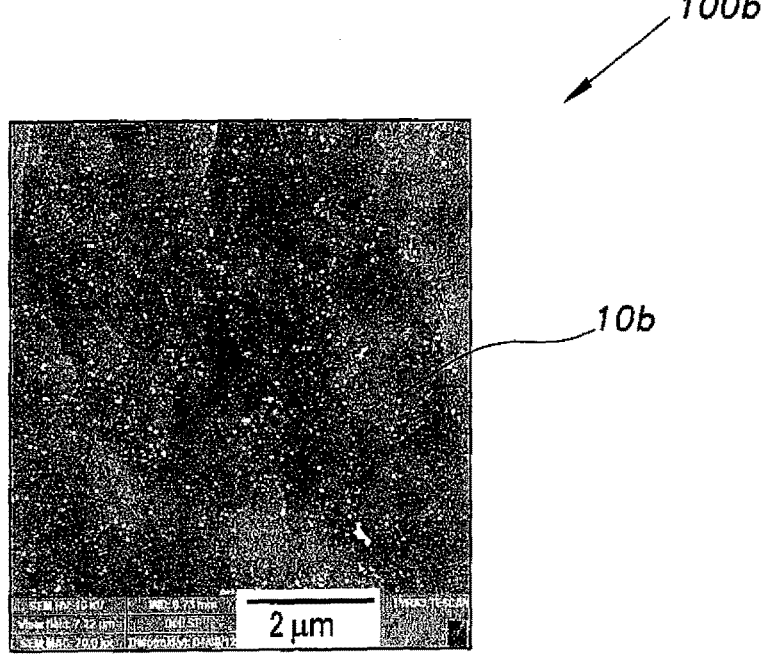
FIG. 1B is a FE-SEM image at 2 μm for an AuNP-GPE electrode according to the present invention.
Figure 1C:
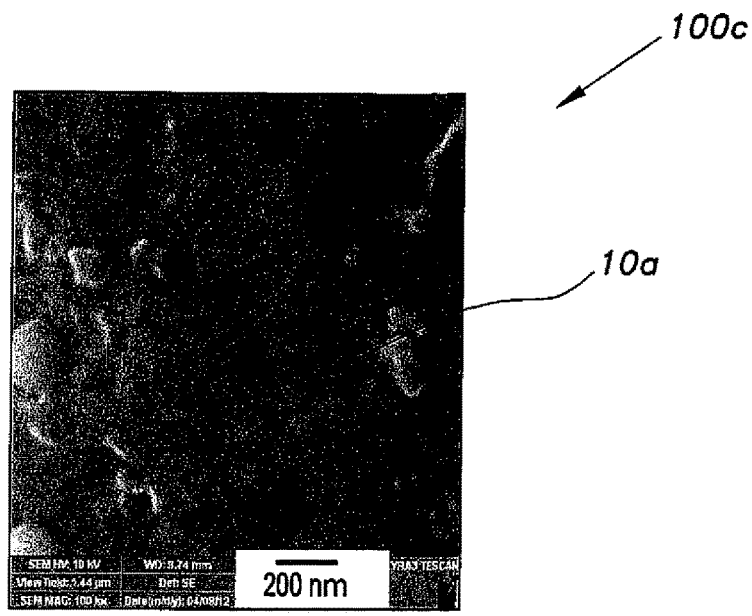
FIG. 1C is a FE-SEM image at 200 nm for a known bare GPE.
Figure 1D:
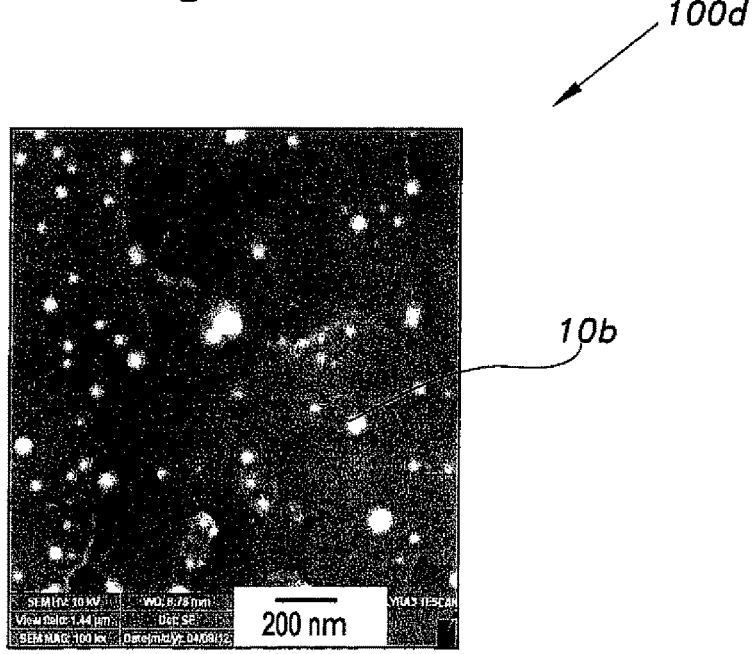
FIG. 1D is a FE-SEM image at 200 nm for an AuNP-GPE according to the present invention.

FIGS. 1A and 1B illustrate 2 μm scanning electron microscope (SEM) images 100a and 100b of the bare GPE 10a and the AuNP-GPE 10b, respectively. Comparing between the SEM images of 100a and 100b, the effect of the presence of AuNP is easily visible. The diameter of the AuNP is in the range of 20-85 nanometers (nm), for example. The low magnification view of the AuNP-GPE 10b indicates that the AuNPs are relatively evenly dispersed on the surface of the GPE. Higher resolution images 100c and 100d of the bare GPE 10a vs. the AuNP-GPE 10b at 200 nm are shown in FIGS. 1C and 1D, respectively.

Figure 2A:
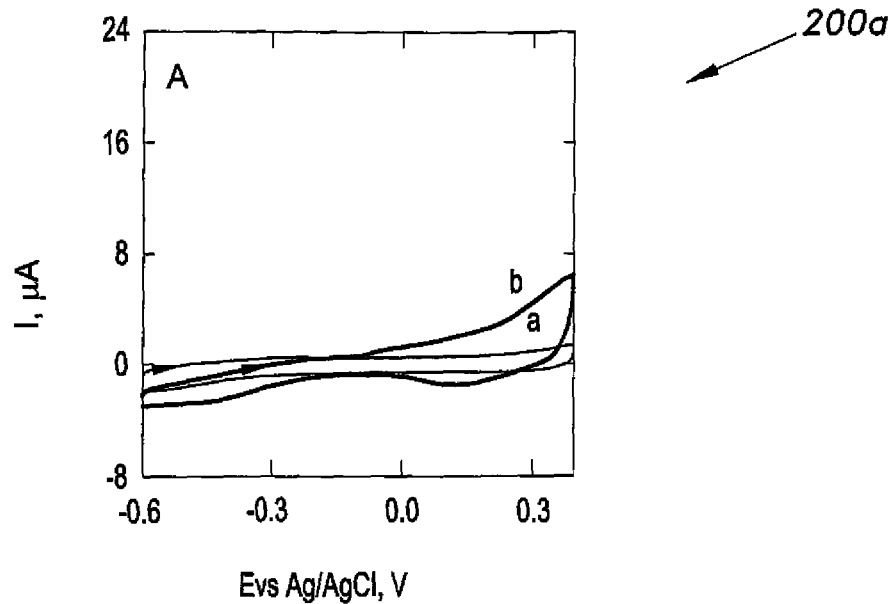
FIG. 2A is a CV plot of a bare GPE versus an AuNP-GPE at a scan rate of 100 millivolts/second (mV/s) in the absence of glucose according to the present invention.
Figure 2B:
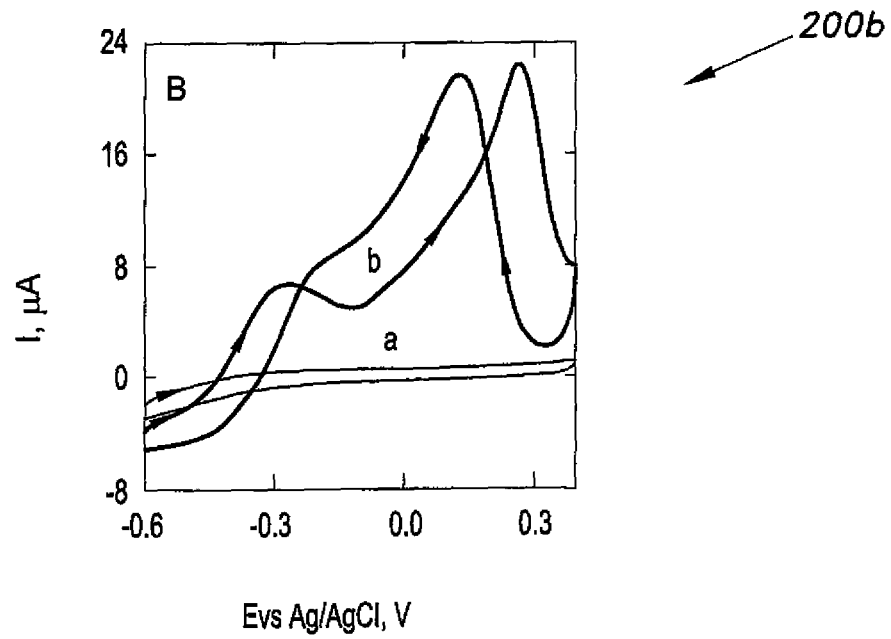
FIG. 2B is a CV plot of a bare GPE versus an AuNP-GPE at a scan rate of 100 mV/s in the presence of glucose according to the present invention.
Figure 2C:
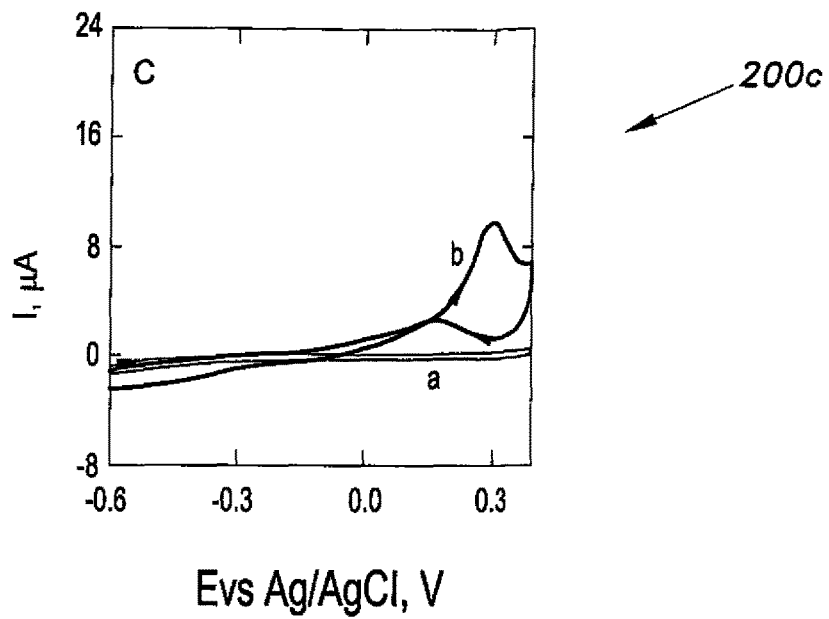
FIG. 2C is a CV plot of a bare GPE versus an AuNP-GPE at a scan rate of 100 mV/s in the presence of fructose according to the present invention.
Figure 2D:
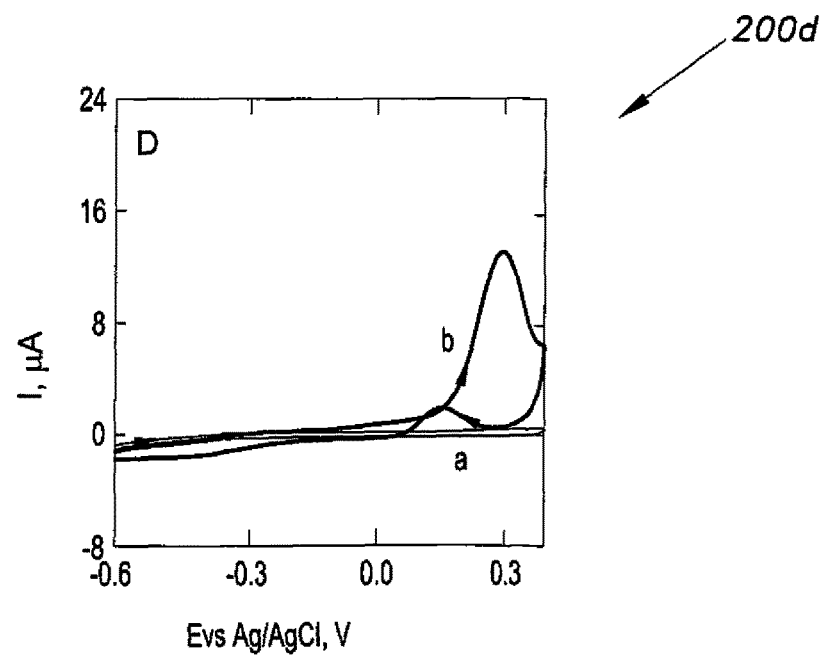
FIG. 2D is a CV plot of a bare GPE versus an AuNP-GPE at a scan rate of 100 mV/s in the presence of sucrose according to the present invention.

With respect to electrocatalytic oxidation of glucose, fructose and sucrose, in FIGS. 2A to 2D, CVs in a 0.1 M NaOH in the absence (FIG. 2A) and presence (FIG. 2B) of 1 mM D-(+) glucose, and in the presence of D-(−) fructose (FIG. 2C), and in the presence of sucrose (FIG. 2D) at a bare GPE ("a" plots in FIGS. 2A to 2D) and at an AuNP-GPE ("b" plots in FIGS. 2A to 2D), and at a scan rate of 100 mV/s are illustrated. Plot 200a of FIG. 2A and plot 200b of FIG. 2B are the CVs in 0.1 M NaOH at a bare GPE and at an AuNP-GPE. In comparison to the CV of bare GPE, it is clear that AuNP-GPE started to oxidize around at −0.1 V in an anodic sweep and the oxidized Au is subsequently reduced at a cathodic sweep with a reduction peak at around +0.12 V, for example. Interestingly, there is relatively no large difference in the background current of an AuNP-GPE and a bare GPE in anodic sweep at <−0.1 V. Therefore, the detection of glucose at <−0.1 V is generally good to obtain a low detection limit, for example. By comparing the "a" line plot of plots 200a-200d in FIGS. 2A through 2D, respectively, it is clear that a bare GPE cannot typically oxidize glucose, fructose, and sucrose in the test potential windows. Moreover, the "b" line plot of plot 200b in FIG. 2B presents the CV of glucose at an AuNP-GPE. From the comparison between the "b" line plot of FIGS. 2A and 2B, it is evident that two peaks at an anodic sweep and one peak at a cathodic sweep appeared for glucose oxidation. This typical glucose electrooxidation behavior in alkaline solution is similar with that at a bulk gold electrode.

While the mechanism of the glucose oxidation is relatively complex, the results of the mechanism in relation to embodiments of an AuNP-GPE, indicate a glucose oxidation peak appears in an anodic sweep at around −0.27 ($E_{pa1}$), and +0.27 V ($E_{pa2}$)) or in a cathodic sweep around at +0.12V ($E_{pc}$). Besides, the oxidation peak of fructose (the "b" line plot in FIG. 2C) or sucrose (the "b" line plot in FIG. 2D) at an AuNP-GPE is in an anodic sweep around at +0.29 V and is in a cathodic sweep around at +0.15V. From the above discussion, it can be determined that in embodiments of an AuNP-GPE, the glucose oxidation peak at −0.27 V is relatively desirable to detect the glucose without any significant interference from fructose and sucrose with a minimum background current which is typically desired to get a low detection limit. However, the glucose oxidation peak current at $E_{pa1}$ is relatively much lower than that obtained at $E_{pa2}$ or $E_{pc}$. Also, a high peak current at $E_{pa1}$ is generally desired for obtaining a low detection limit with a relatively high selectivity.

Referring to FIGS. 3A to 3D, CVs in 0.1 M NaOH in the absence (FIG. 3A and FIG. 3C) and presence (FIG. 3B and FIG. 3D) of a 1 mM D-(+) glucose at a bare GPE (FIG. 3A and FIG. 3B) and at an AuNP-GPE (FIG. 3C and FIG. 3D) at a scan rate of 100 mV/s are illustrated. The CVs in FIGS. 3A-3D were recorded before (plots "a") and after (plots "b") cathodization of the electrodes at −1.0 V for 60 s. Regarding glucose oxidation signal enhancement by cathodization of AuNP-GPE in relation to embodiments of an AuNP-GPE, initially, the cathodization effect on background current of a bare GPE, as shown in plot 300a of FIG. 3A and an AuNP-GPE, as shown in plot 300c of FIG. 3C was checked. By comparing the "a" plot line and the "b" plot line of plot 300a in FIG. 3A, it is observed that there was no significant change in a background current before and after cathodization of a bare GPE. Similarly, no significant change is found in a background current of a cathodized ("b" plot line of plot 300c in FIG. 3C) and uncathodized ("a" plot line of plot 300c in FIG. 3C) AuNP-GPE.

Figure 3A:
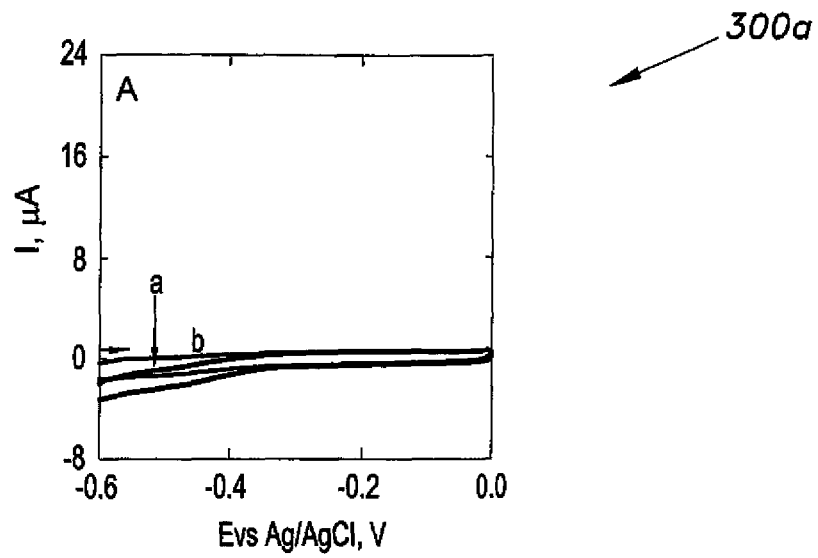
FIG. 3A is a plot of CVs in the absence of glucose at a bare GPE, before versus after cathodization. Scan rate: 100 mV/s.
Figure 3B:
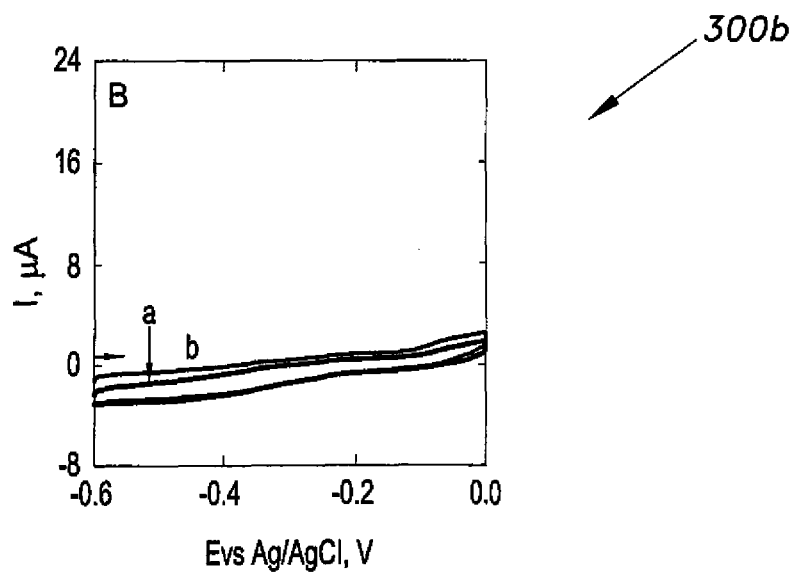
FIG. 3B is a plot of CVs in the presence of glucose at a bare GPE before versus after cathodization. Scan rate: 100 mV/s.
Figure 3C:
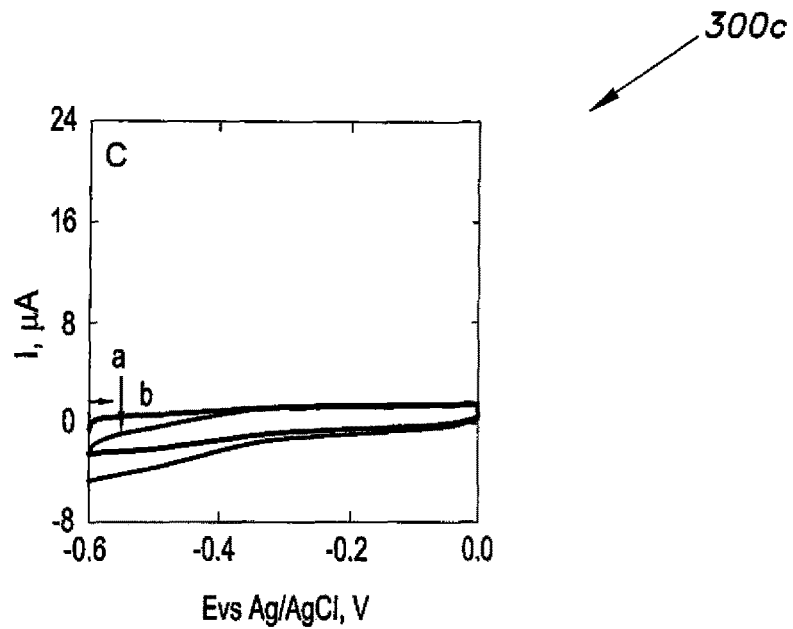
FIG. 3C is a plot of CVs in the absence of glucose at an AuNP-GPE, before versus after cathodization, at a scan rate of 100 mV/s.
Figure 3D:
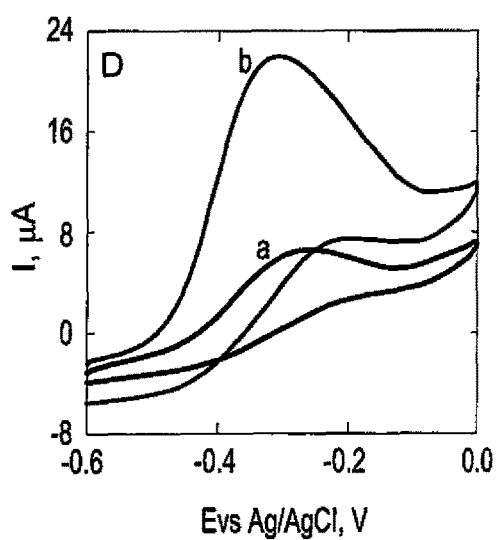
FIG. 3D is a plot of CVs in the presence of glucose at an AuNP-GPE, before versus after cathodization. Scan rate: 100 mV/s.

As evident from the "b" CV plots of FIGS. 3A and 3C, the background current of a cathodized bare GPE and of a cathodized AuNP-GPE is similar. Also, a cathodized and an uncathodized bare GPE typically cannot oxidize glucose at negative potential, which is confirmed by comparing the "b" plot lines of FIGS. 3A and 3B. Comparing FIGS. 3C and 3D and the "b" plot line of FIG. 2B shows that glucose can be oxidized on uncathodized or cathodized AuNP-GPE at around −0.27 V. However, the signal of glucose electrooxidation has been enhanced significantly at an AuNP-GPE after cathodization (the "b" plot line of plot 300d in FIG. 3D) compared to that of before cathodization (the "b" plot line of FIG. 2B and the "a" plot line of FIG. 3D), for example.

Figure 4A:
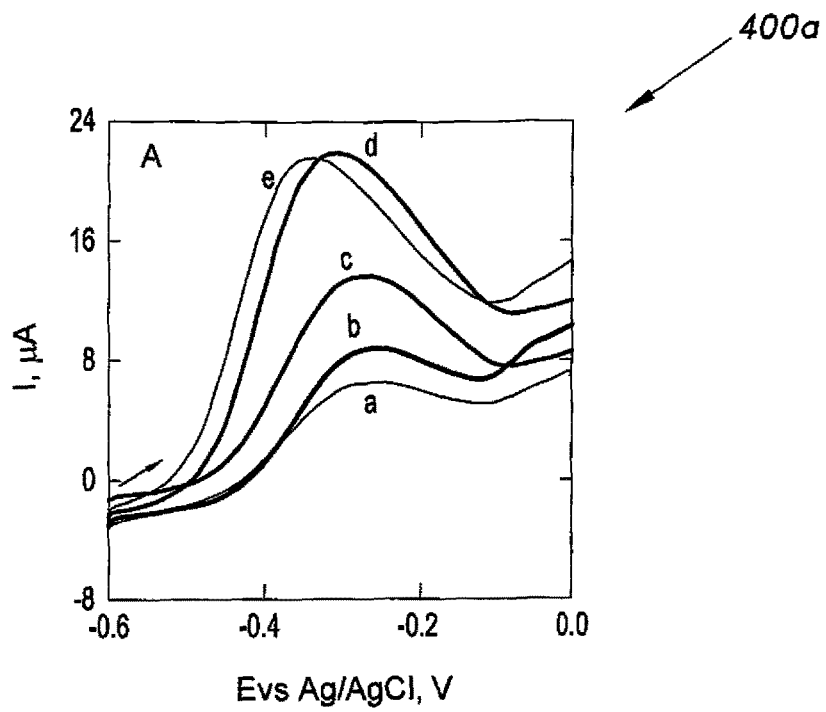
FIG. 4A is a plot of anodic sweeps of CVs in the presence of glucose at an AuNP-GPE after cathodization at different potentials. Scan rate: 100 mV/s.
Figure 4B:
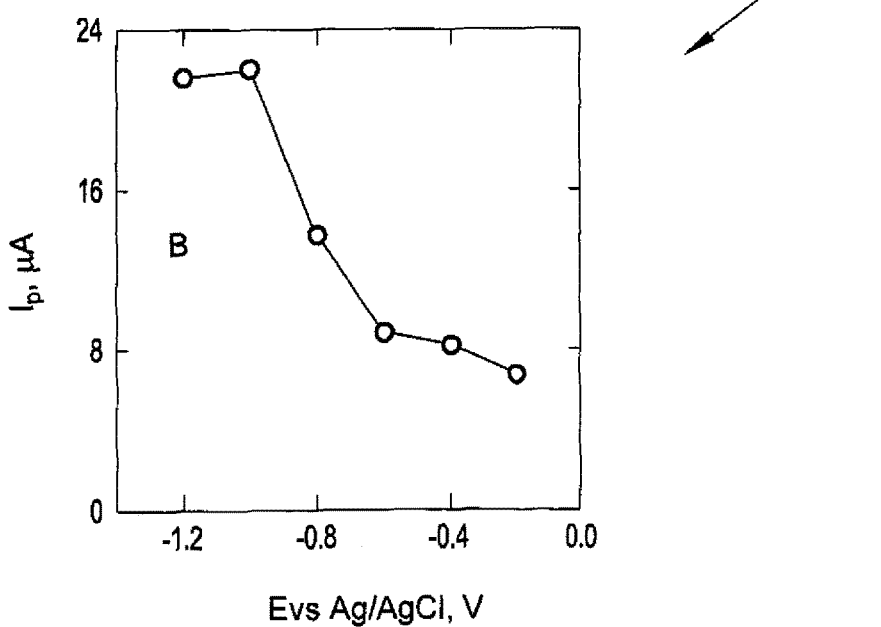
FIG. 4B is a plot of peak current versus cathodization potential of FIG. 4A.

With respect to optimization of cathodization parameters for glucose oxidation, to obtain a highest signal of glucose, the cathodization potential and time were optimized. Referring to FIG. 4A, anodic sweeps of CVs in a 0.1 M NaOH containing 1 mM D-(+) glucose at an AuNP-GPE, after cathodization for 60 s at different potentials of (a) −0.2 V, (b) 0.6 V, (c) −0.8 V, (d) −1.0 V and (e) −1.2 V, and a scan rate of 100 mV/s are illustrated; and FIG. 4B illustrates the corresponding plot of peak current vs. cathodization potential. Plot 400a of FIG. 4A illustrates an anodic sweep of CVs of 1 mM glucose which were obtained at an AuNP-GPE after cathodization at different potentials for 60 seconds in the same glucose solution. Plot 400b of FIG. 4B illustrates the corresponding plot of peak current versus cathodization potential. This plot indicates that −1.0 V is a desirable cathodization potential for achieving a relatively highest signal of glucose, for example.

Figure 5A:
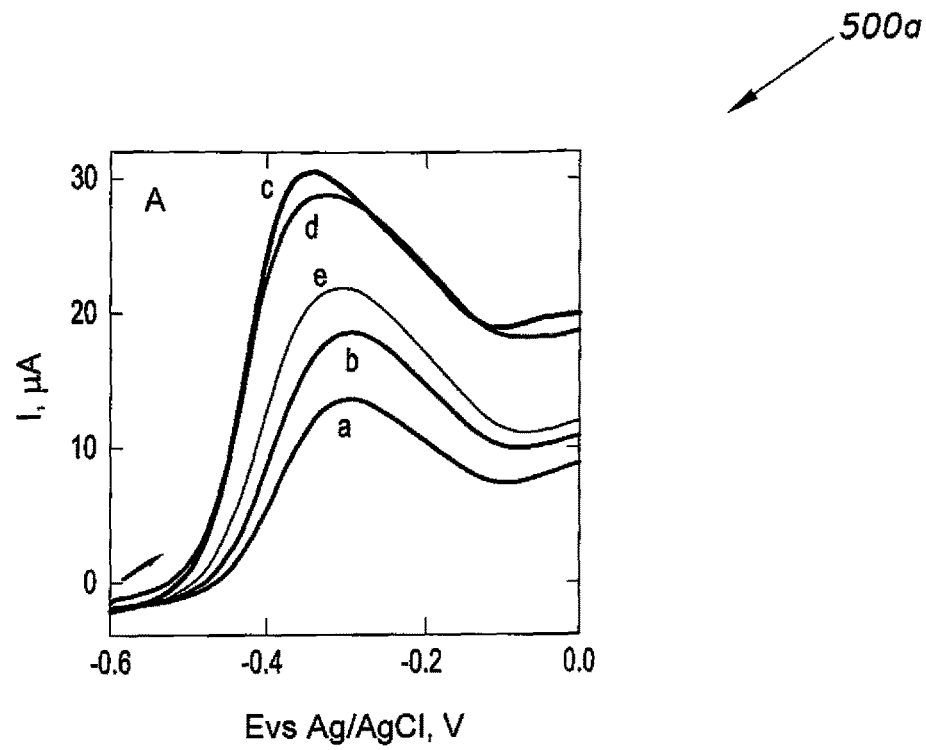
FIG. 5A is a plot of anodic sweeps of CVs in the presence of glucose at an AuNP-GPE after cathodization at different times.
Figure 5B:
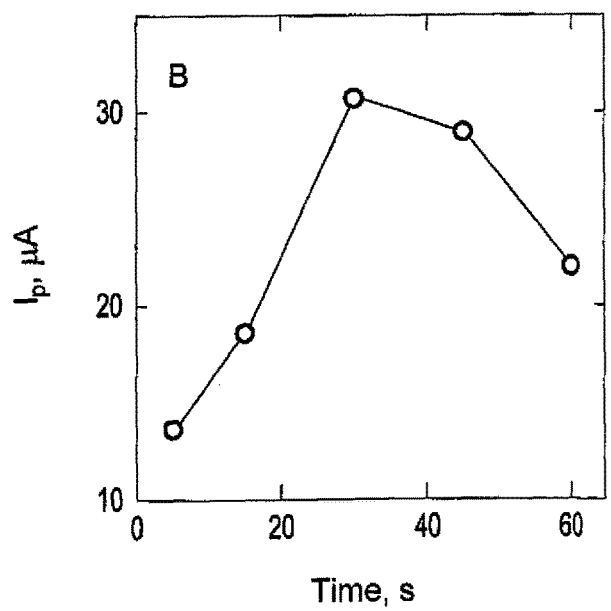
FIG. 5B is a plot of peak current versus cathodization time of FIG. 5A.

Referring to FIG. 5A, anodic sweeps of CVs in a 0.1 M NaOH containing 1 mM D-(+) glucose at an AuNP-GPE after cathodization at −1.0 V for different times of (a) 5 s, (b) 15 s, (c) 30 s, (d) 45 s and (e) 60 s, at a scan rate of 100 mV/s are illustrated; and FIG. 5B illustrates the corresponding plot of peak current versus cathodization time. Plot 500a of FIG. 5A indicates an anodic sweep of CVs of 1 mM glucose which were obtained at AuNP-GPE after cathodization at −1.0 V for the different times "a" through "e" in the same glucose solution. The plot of peak current versus cathodization time (plot 500b of FIG. 5B) indicates that the relatively highest signal was obtained at an AuNP-GPE after cathodization at −1.0 V for 30 seconds. As a result, −1.0 V and 30 seconds were selected for cathodization of an AuNP-GPE in further experiments.

Figure 6A:
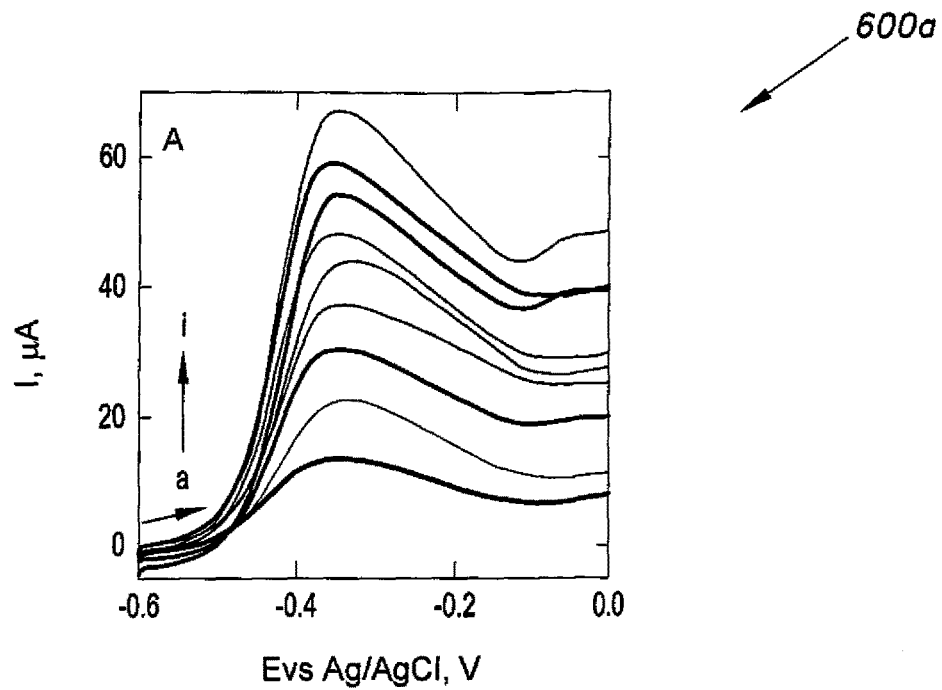
FIG. 6A is a plot of anodic sweeps of CVs at different scan rates in the presence of glucose at a cathodized AuNP-GPE.
Figure 6B:
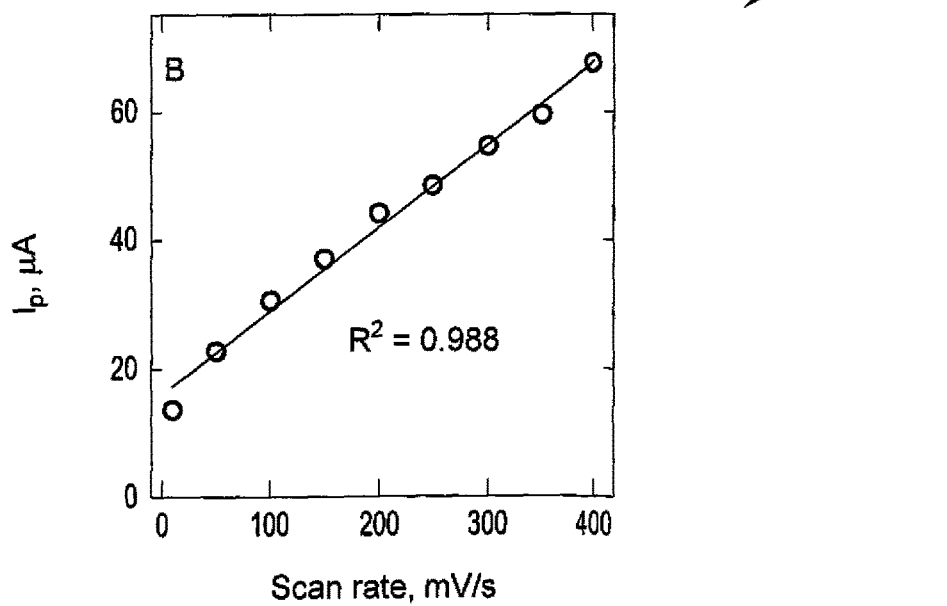
FIG. 6B is a plot of peak current versus scan rate of FIG. 6A.

Referring to FIG. 6A, anodic sweeps of CVs in a 0.1 M NaOH containing 1 mM D-(+) glucose at an AuNP-GPE after cathodization at −1.0 V for 30 s at scan rates of (a) 10 mV/s, (b) 50 mV/s, (c) 100 mV/s, (d) 150 mV/s, (e) 200 mV/s, (f) 250 mV/s, (g) 300 mV/s, (h) 350 mV/s and (i) 400 mV/s are illustrated; and FIG. 6B illustrates the corresponding plot of peak current versus scan rate. Regarding the effect of scan rate on glucose oxidation in relation to embodiments of an AuNP-GPE, the relationship between peak current and scan rate can be described as to the electrochemical mechanism. Therefore, anodic sweeps of CVs of 1 mM glucose at a cathodized AuNP-GPE were recorded at different scan rates from 10-400 mV/s (plot 600a of FIG. 6A, at the scan rates "a" through "i"). Plot 600b of FIG. 6B shows the corresponding plot of peak current vs. scan rate. This plot shows that peak current has been linearly increased with increasing the scan rate. The plot follows the linear equations $I_p$ (µA)=0.13v (V/s)+15.92; $R^2$=0.988. This indicates that the electrode process was controlled by adsorption rather than diffusion, for example.

The reproducibility of the embodiments of glucose sensing methods using embodiments of a cathodized AuNP-GPE was verified by recording the CVs at a scan rate of 300 mV/s in a 0.1 M NaOH containing 1 mM glucose at a series of modified AuNP-GPE electrode surfaces after pretreatment at −1.0 V for 30 seconds. The intraday experiments showed a peak current of 49.128±4.7190 µA (mean±standard deviation) with a relative standard deviation of 9.6%, whereas the interday experiments showed a peak current of 49.357±4.652 µA with a relative standard deviation of 9.43%. The results indicate that embodiments of a glucose sensing method using embodiments of a cathodized AuNP-GPE are reproducible.

Regarding the effect of presence or absence of glucose during cathodization, an AuNP-GPE was cathodized in a 0.1 M NaOH containing 1 mM glucose solution, followed by recording the CV of glucose oxidation in the same solution. However, to compare the effect of glucose toward the glucose oxidation reaction if the electrode is cathodized in the absence of an analyte, the AuNP-GPE was also cathodized only in 0.1 M NaOH at −1.0 V for 30 seconds. Afterward, 1 mM equivalent amount of glucose solution was added to the 0.1 M NaOH. A comparison of the results indicates that a substantially same level of the glucose oxidation signal was obtained for both cases. These phenomena indicate that cathodization of an AuNP-GPE changes the electrocatlytic properties for the enhancing of the glucose oxidation signal, rather than the accumulation of glucose during the negative potential treatment.

Figure 7A:
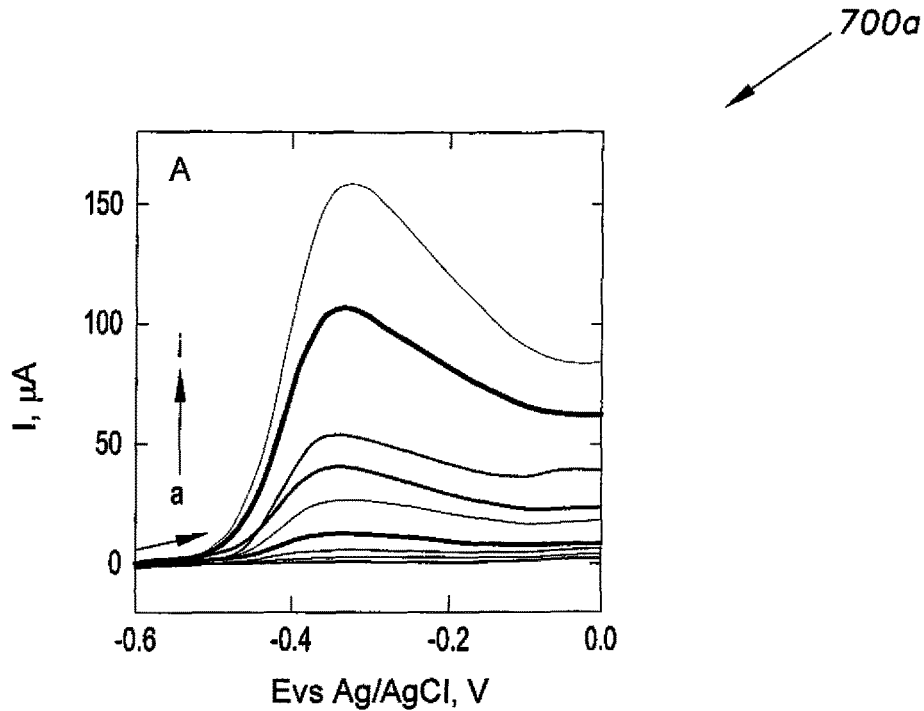
FIG. 7A is a plot of anodic sweeps of CVs in the presence of various concentrations of glucose at a cathodized AuNP-GPE.
Figure 7B:
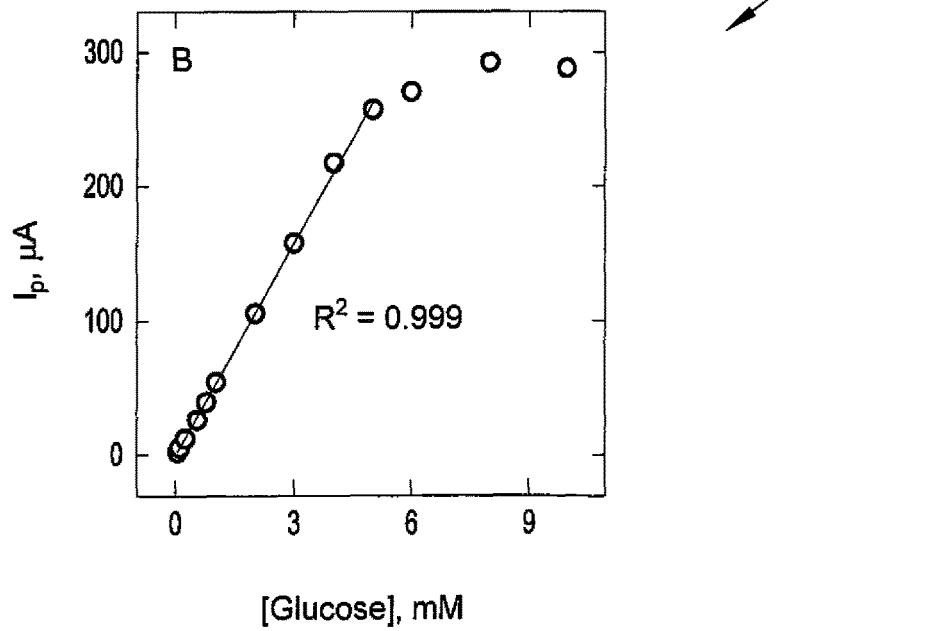
FIG. 7B is the corresponding calibration curve of FIG. 7A.

Referring to FIG. 7A, anodic sweeps of CVs in a 0.1 M NaOH containing different mM concentrations of D-(+) glucose at an AuNP-GPE after cathodization at −1.0 V for 30 s, at (a) 0.0 mM, (b) 0.05 mM, (c) 0.1 mM, (d) 0.25 mM, (e) 0.50 mM, (f) 0.75 mM, (g) 1.0 mM, (h) 2.0 mM and (i) 3.0 mM D-(+) glucose at a scan rate of 300 mV/s are illustrated; and FIG. 7B illustrates the corresponding calibration curve. With respect to voltammetric determination of glucose the glucose concentration-dependent CVs (plot 700a of FIG. 7A at the concentrations "a" through "i") were recorded at an AuNP-GPE after cathodization in the respective glucose solution at −1.0 V for 30 seconds to determine the limit of detection.

The concentration dependence calibration curve (plot 700b of FIG. 7B) was constructed from the signal after subtracting the mean of the zero glucose response. The calibration plot shows that the glucose oxidation signals increase linearly with increasing concentration of glucose in a range between 0.05 mM to 5 mM. The calibration plot follows the linear regression equations, $I_p$=52.613 [glucose]+0.2066; $R^2$=0.999. However, a further increase of the concentration to more than 5 mM results in the signal showing a non linear behavior with concentration. The calculated limit of detection at 3σ was 12 µM glucose, for example. This limit of detection is comparable for a glucose sensor based on the Au nanomaterial-modified carbon electrode, for example.

Figure 8A:
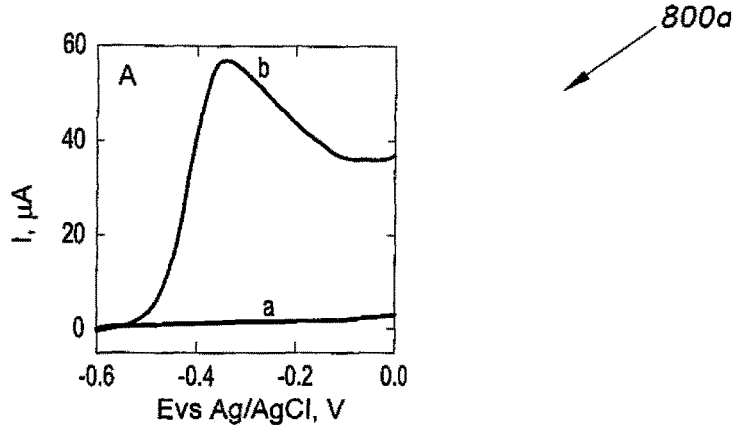
FIG. 8A is a plot of anodic sweeps of CVs of fructose in the absence and presence of glucose at a cathodized AuNP-GPE.
Figure 8B:
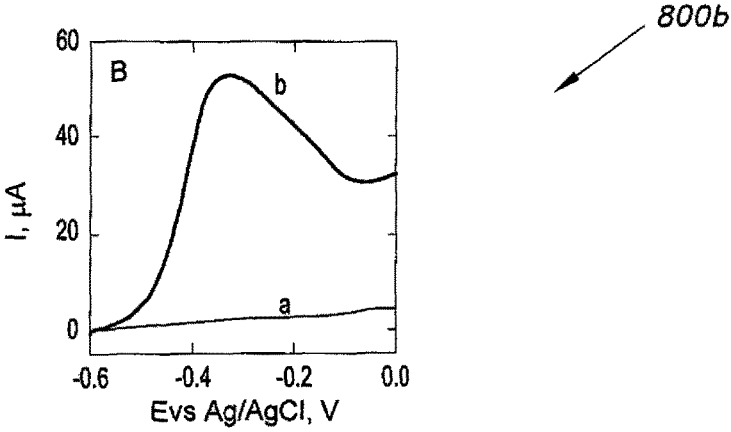
FIG. 8B is a plot of anodic sweeps of CVs of sucrose in the absence and presence of glucose at a cathodized AuNP-GPE.
Figure 8C:
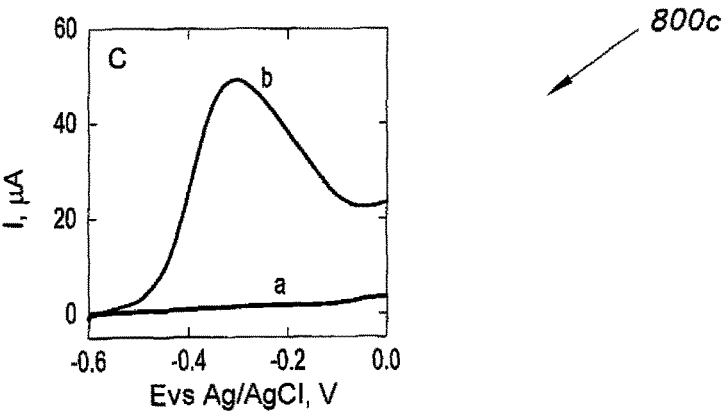
FIG. 8C is a plot of anodic sweeps of CVs of sodium chloride in the absence and presence of glucose at a cathodized AuNP-GPE.

Fructose, sucrose and NaCl coexist with glucose in many samples including food and drugs. The fructose, glucose and NaCl can potentially interfere with the glucose oxidation signal. Therefore, the effects of the presence of a 1 mM fructose or sucrose or NaCl on oxidation of 1 mM glucose at embodiments of an AuNP-GPE after cathodization in the respective glucose solution at −1.0 V for 30 seconds were studied. Referring to FIGS. 8A to 8C, anodic sweeps of CVs in a 0.1 M NaOH containing 0.1 mM D-(−) fructose (FIG. 8A) in the absence (plot "a") and presence (plot "b") of a 1 mM D-(+) glucose, a 0.1 mM sucrose (FIG. 8B) in the absence (plot "a") and presence (plot "b") of a 1 mM D-(+) glucose, a 1 mM NaCl (FIG. 8C) in the absence (plot "a") and presence (plot "b") of a 1 mM D-(+) glucose at an AuNP-GPE after cathodization at −1.0 V for 30 s and at a scan rate of 300 mV/s are illustrated.

The "a" plot line shown in plots 800a, 800b, and 800c of FIGS. 8A, 8B and 8C, respectively, depicts the anodic sweeps of CVs of 1 mM fructose, sucrose and NaCl, respectively. The CV data shows that fructose, sucrose and NaCl typically cannot generate any signal in the tested potential windows, whereas a 1 mM glucose in the absence (plot "g" of FIG. 7A) or presence of 1 mM fructose (plot "b" of FIG. 8A) or sucrose (plot "b" of FIG. 8B) or NaCl (plot "b" of FIG. 8C) can generate similar glucose oxidation signals. The results indicate that embodiments of a method using embodiments of an AuNP-GPE are valid for the detection of glucose in the presence of fructose, sucrose and NaCl without any substantial inference.

Embodiments of a cathodized AuNP-GPE provide a sensitive, selective, relatively inexpensive and disposable glucose sensor based on a cathodized AuNP-GPE. The cathodized AuNP-GPE shows relatively superior electrocatalytic properties toward electroxidation of glucose compared to an uncathodized AuNP-GPE or a bare GPE. The selectivity of the glucose sensor was obtained by selecting the appropriate potential windows of a CV. A limit of detection of the embodiments of the AuNP-GPE sensor is 12 µM of glucose, for example. For a significantly low detection limit, greater analytical selectivity and sensitivity and relatively low cost, embodiments of a method using embodiments of a cathodized AuNP-GPE based on cathodization of a relatively simply prepared AuNP-GPE can be suitable for analytical determination of glucose in various fields.

It is to be understood that the present invention is not limited to the embodiments described above, but encompasses any and all embodiments within the scope of the following claims.

We claim:

1. A method for forming a cathodized gold nanoparticle graphite electrode, comprising the steps of:
    placing a solid graphite member into a tube filled with a prepared solution of L-ascorbic acid (AA) and Gold (III) chloride;
    placing the filled tube and solid graphite member combination into a water bath preheated to approximately 75° centigrade (C.);

retaining said filled tube and solid graphite member combination in said water bath for approximately 15 minutes to form a gold nanoparticle graphite electrode (AuNP-GPE);

removing said solid graphite member from said tube, said solid graphite member being transformed into said AuNP-GPE;

washing said AuNP-GPE in deionized water;

drying said AuNP-GPE at approximately 60° C. for approximately 5 minutes prior to use; and cathodizing said AuNP-GPE by placing said AuNP-GPE in a basic solution and applying −1.0 volts to said AuNP-GPE for approximately 30 seconds.

2. The method for forming a cathodized gold nanoparticle graphite electrode according to claim 1, wherein said basic solution is a glucose analyte solution.

3. The method for forming a cathodized gold nanoparticle graphite electrode according to claim 1, wherein said basic solution consists essentially of NaOH.

4. The method for forming a cathodized gold nanoparticle graphite electrode according to claim 1, wherein said basic solution includes NaOH and glucose.

5. The method for forming a cathodized gold nanoparticle graphite electrode according to claim 1, wherein said basic solution consists essentially of a 0.1 molar (M) NaOH including glucose.

6. The method for forming a cathodized gold nanoparticle graphite electrode according to claim 1, further comprising the step of:

preparing said AA and Gold (III) chloride solution in equal volumes, approximately 1.5 milliliters (ml) of each aqueous solutions of approximately 1.65 millimolar (mM) AA and 1.0 mM Gold(III) chloride, wherein said tube is approximately 3.0 ml in volume.

7. The method for forming a cathodized gold nanoparticle graphite electrode according to claim 1, wherein said solid graphite member is a mechanical pencil lead.

8. The method for forming a cathodized gold nanoparticle graphite electrode according to claim 7, wherein said mechanical pencil lead is a hi-polymer graphite pencil HB grade lead.

9. The method for forming a cathodized gold nanoparticle graphite electrode according to claim 7, further comprising the step of:

fixing an electrically conductive holder of said mechanical pencil lead vertically with 15 millimeters (mm) of said mechanical pencil lead extruded outside said electrically conductive holder and 10 mm of said mechanical pencil lead immersed in a glucose analyte solution as said basic solution, maintaining a geometric electrode area of approximately 15.90 mm$^2$.

10. The method for forming a cathodized gold nanoparticle graphite electrode according to claim 1, wherein placement of said solid graphite member into the tube of AA and Gold(III) chloride chemically deposits gold nanoparticles in the range of 20-85 nanometers (nm) on said solid graphite member.

* * * * *